(12) United States Patent
Morey et al.

(10) Patent No.: US 11,672,598 B2
(45) Date of Patent: Jun. 13, 2023

(54) MEDICAL SYSTEMS, DEVICES, AND RELATED METHODS

(71) Applicant: Boston Scientific Limited, Hamilton (BM)

(72) Inventors: Subodh Morey, Goa (IN); Rajivkumar Singh, Maharashtra (IN); Arun Adhikarath Balan, Kerala (IN); Niraj P. Rauniyar, Plymouth, MN (US); Brian P. Watschke, Minneapolis, MN (US); Aditi Ray, San Jose, CA (US); Thomas C. Hasenberg, Campbell, CA (US); Kenneth P. Reever, Hopedale, MA (US)

(73) Assignee: Boston Scientific Limited, Hamilton (BM)

( * ) Notice: Subject to any disclaimer, the term of this patent is extended or adjusted under 35 U.S.C. 154(b) by 270 days.

(21) Appl. No.: 17/028,196

(22) Filed: Sep. 22, 2020

(65) Prior Publication Data

US 2021/0085394 A1 Mar. 25, 2021

Related U.S. Application Data

(60) Provisional application No. 62/905,028, filed on Sep. 24, 2019.

(51) Int. Cl.
*A61B 18/20* (2006.01)
*A61B 18/22* (2006.01)
*A61B 18/00* (2006.01)

(52) U.S. Cl.
CPC .... *A61B 18/22* (2013.01); *A61B 2018/00077* (2013.01); *A61B 2018/00589* (2013.01);
(Continued)

(58) Field of Classification Search
CPC .......... A61N 18/00; A61N 18/20; A61N 5/06
See application file for complete search history.

(56) References Cited

U.S. PATENT DOCUMENTS

| 4,185,933 A | * | 1/1980 | Zepell | ................... B43K 24/10 |
|---|---|---|---|---|
| | | | | 401/63 |
| 5,312,399 A | | 5/1994 | Hakky et al. | |

(Continued)

FOREIGN PATENT DOCUMENTS

| CN | 1205620 A | 1/1999 |
|---|---|---|
| CN | 106725830 A | 12/2016 |

(Continued)

OTHER PUBLICATIONS

International Search Report and Written Opinion issued in International Application No. PCT/IB2020/058853, dated Dec. 7, 2020 (13 pages).

*Primary Examiner* — Lynsey C Eiseman
(74) *Attorney, Agent, or Firm* — Bookoff McAndrews, PLLC

(57) ABSTRACT

A medical system includes an insertion device including a handle and a delivery portion, a laser fiber, a conductive wire, and a lock. The laser fiber extends through the insertion device and is coupled to a laser slider to control a position of the laser fiber relative to a distal end of the delivery portion. The conductive wire extends through the insertion device and is coupled to a wire slider to control a position of the laser fiber relative to a distal end of the delivery portion. The lock is positioned within the handle and is movable in order to selectively lock either the movement of the laser slider or lock the movement of the wire slider.

13 Claims, 6 Drawing Sheets

(52) U.S. Cl.
CPC ............... *A61B 2018/00595* (2013.01); *A61B 2018/00625* (2013.01); *A61B 2018/00696* (2013.01); *A61B 2018/00946* (2013.01); *A61B 2018/2015* (2013.01)

(56) References Cited

U.S. PATENT DOCUMENTS

| | | | |
|---|---|---|---|
| 5,534,000 A | 7/1996 | Bruce | |
| 5,876,373 A * | 3/1999 | Giba | A61M 25/0136 604/95.04 |
| 6,174,307 B1 * | 1/2001 | Daniel | A61B 1/00098 606/7 |
| 9,844,410 B2 | 12/2017 | Mitchell et al. | |
| 10,251,703 B2 | 4/2019 | Albeck et al. | |
| 2014/0012077 A1 | 1/2014 | Fagnani | |
| 2014/0107630 A1 * | 4/2014 | Yeik | A61F 9/008 606/5 |
| 2015/0088130 A1 * | 3/2015 | Sekino | A61B 17/3203 606/46 |
| 2015/0150633 A1 * | 6/2015 | Castro | A61B 17/29 606/130 |
| 2017/0119470 A1 | 5/2017 | Diamant et al. | |
| 2018/0303548 A1 | 10/2018 | Brown et al. | |

FOREIGN PATENT DOCUMENTS

| | | |
|---|---|---|
| EP | 2881059 | 6/2015 |
| WO | WO 2017011542 | 1/2017 |

\* cited by examiner

MEDICAL SYSTEMS, DEVICES, AND RELATED METHODS

CROSS-REFERENCE TO RELATED APPLICATIONS

This patent claims the benefit of priority under 35 U.S.C. § 119 to U.S. Provisional Patent Application No. 62/905,028, filed Sep. 24, 2019, which is herein incorporated by reference in its entirety.

TECHNICAL FIELD

Various aspects of the present disclosure relate generally to medical systems, devices, and related methods. More specifically, the present disclosure relates to medical systems, devices, and methods for delivering laser energy and delivering electrical energy in a medical procedure.

BACKGROUND

Medical lasers have been utilized in a variety of treatment procedures including, for example, urology, neurology, otorhinolaryngology, general anesthetic ophthalmology, dentistry, gastroenterology, cardiology, gynecology, and thoracic and orthopedic procedures. These procedures often require precisely controlled and directed delivery of energy in order to successfully accomplish the desired procedure. Generally, a surgical probe is utilized to deliver laser energy to the body. The surgical probe often includes an optical fiber coupled to a laser source wherein the probe can be positioned such that the tip of the probe is positioned adjacent the targeted tissue. Laser energy is directed out of the tip of the optical fiber onto desired portions of the targeted tissue.

The medical professional performing the particular procedure manipulates the optical fiber into position near the targeted tissue and sets the laser power and mode for treatment of the targeted tissue. There are times when the power and mode settings must be changed from one mode to another mode if there is bleeding present and the laser is to be used to stop the bleeding. However, some laser sources and/or laser fibers are not suited to deliver energy to coagulate or otherwise stop bleeding. In these aspects, the user may need to remove the laser fiber and introduce another energy delivery or treatment device to help stop bleeding or otherwise treat the tissue. Manually changing between devices can be time-consuming, especially in the midst of performing treatment. Additionally, removing one device and delivering another device may increase the risk of injury, complicate the procedure, increase the stresses on the user, and otherwise increase the risk and duration of a procedure.

The systems, devices, and methods of the current disclosure may rectify some of the deficiencies described above, and/or address other aspects of the prior art.

SUMMARY

Examples of the present disclosure relate to, among other things, medical systems, devices, and methods. Each of the examples disclosed herein may include one or more of the features described in connection with any of the other disclosed examples.

In one example, a medical system may include an insertion device including a handle and a delivery portion, a laser fiber, a conductive wire, and a lock. The laser fiber may extend through the insertion device and may be coupled to a laser slider to control a position of the laser fiber relative to a distal end of the delivery portion. The conductive wire may extend through the insertion device and may be coupled to a wire slider to control a position of the conductive wire relative to a distal end of the delivery portion. The lock may be positioned within the handle and may be movable in order to selectively lock either the movement of the laser slider or the movement of the wire slider.

The medical system may include one or more of the following aspects. The lock may include first and second side arms. In a first configuration, a first side arm may extend from a first side of the handle, and a second side arm may be within or aligned with a second side of the handle opposite to the first side. In a second configuration, the second side arm may extend from the second side of the handle, and the first side arm may be within or aligned with the first side of the handle. The lock may include a forward arm and a rear arm. The forward arm and the rear arm may be laterally offset from one another. In the first configuration, the forward arm may block the wire slider from moving distally in order to limit distal movement of the conductive wire and may allow the laser slider and the laser fiber to move distally. In the second configuration, the rear arm may block the laser slider from moving distally in order to limit distal movement of the laser fiber and may allow the wire slider and the conductive wire to move distally.

The medical system may further include a spring within the handle to bias distal movement of the wire slider. The wire slider may include a rod portion that extends distally through a portion of the spring, and the rod portion may limit the distal extension of the wire slider. The laser fiber may include a distal end cap to direct laser energy. The distal end cap may include a side opening to form a side-fire distal end. The laser slider may be movably positioned on a top portion of the handle, and the wire slider may be movably positioned on a bottom portion of the handle. A proximal end of the laser fiber may be configured to be coupled to a laser energy source, and a proximal end of the conductive wire may be configured to be coupled to an electrical energy source. The medical system may further include a first actuator configured to control the delivery of laser energy from the laser energy source to the laser fiber and a second actuator configured to control the delivery of electrical energy from the electrical energy source to the conductive wire. The laser fiber may be configured to deliver up to 180 W of 532 nm light.

In another example, a medical device may include a handle, a delivery portion extending from the handle, a first slider movably coupled to the handle and configured to control movement of a first energy delivery device, a second slider movably coupled to the handle and configured to control movement of a second energy delivery device, and a lock at least partially positioned within the handle. The lock may be movable between a first position in which a portion of the lock blocks distal movement of the first slider, and a second position in which a portion of the lock blocks distal movement of the second slider.

The medical device may include one or more of the following aspects. The medical device may further include a spring coupled to a distal end of the second slider to bias the distal movement of the second slider. The lock may include first and second side arms, a forward arm, and a rear arm. In the first configuration, a first side arm may extend from a first side of the handle and a second side arm may be within or aligned with a second side of the handle opposite to the first side. In the second configuration, the second side arm may extend from the second side of the handle and the first side arm may be within or aligned with the first side of the handle. The forward arm and the rear arm may be laterally offset from one another such that, in the first configuration, the forward arm may block the wire slider from moving distally in order to limit distal movement of the conductive wire and may allow the laser slider and the laser fiber to move distally. In the second configuration, the rear arm may block the laser slider from moving distally in order to limit distal movement of the laser fiber and may allow the wire slider and the conductive wire to move distally.

In yet another example, a method of delivering treatment to a treatment site may include positioning a distal end of a delivery portion of a medical device at the treatment site. The delivery portion may be coupled to a handle that includes a laser slider, a wire slider, and a lock. The laser slider may be coupled to a laser fiber and controllable to extend or retract the laser fiber from the distal end of the delivery portion. The wire slider may be coupled to a conductive wire and controllable to extend or retract the conductive wire from the distal end of the delivery portion. The lock may be movable to selectively limit the distal movement of one of either the laser slider or the wire slider. The method may further include positioning the lock in a first position in which the lock blocks the distal movement of the wire slider, extending the laser fiber by moving the laser slider distally, delivering laser energy to the treatment site through the laser fiber to vaporize tissue, retracting the laser fiber by moving the laser slider proximally, positioning the lock in a second position in which the lock blocks the lock blocks the proximal movement of the laser slider, extending the conductive wire by moving the wire slider distally, and delivering electrical energy to the treatment site through the conductive wire to cauterize or coagulate tissue.

The method may include one or more the following aspects. The lock may include two side arms and forward and rear arms. The forward and rear arms may be laterally offset from one another, and the lock may be movable between the first position and the second position by pushing one of the side arms to be within or align with a side of the handle.

BRIEF DESCRIPTION OF THE FIGURES

The accompanying drawings, which are incorporated in and constitute a part of this specification, illustrate various exemplary embodiments and, together with the description, serve to explain the principles of the disclosure.

DETAILED DESCRIPTION

Examples of the present disclosure include systems, devices, and methods to facilitate, and improve the efficacy and safety of minimally-invasive surgeries. For example, aspects of the present disclosure may relate to medical devices and methods for delivering laser energy and electrical energy during a medical procedure with a medical device, such as, for example, a procedure to treat tissue. In some embodiments, the medical systems, devices, and methods of the present disclosure may be used to treat a patient's prostate, for example, to treat benign prostatic hyperplasia ("BPH"), or prostate gland enlargement, which can lead to uncomfortable urinary symptoms, blockages of the flow of urine from the bladder, along with other bladder, urinary tract, or kidney issues. The medical systems, devices, and methods of the present invention may be used with a system for Photoselective Vaporization of the Prostate ("PVP") (e.g., GreenLight™ Laser Therapy by Boston Scientific Corp.), a laser system for the treatment of soft tissues, particularly, a laser system for the PVP or evaporation of prostate tissue in the treatment of BPH. The PVP system may be used to deliver energy to vaporize or evaporate tissue that is causing a blockage in the flow of urine in order to clear the blockage. The PVP therapy systems are generally described in U.S. Pat. Nos. 6,554,824 and 6,986,764, which are hereby incorporated by reference in their entirety.

Reference will now be made in detail to examples of the present disclosure described above and illustrated in the accompanying drawings. Wherever possible, the same reference numbers will be used throughout the drawings to refer to the same or like parts.

The terms "proximal" and "distal" are used herein to refer to the relative positions of the components of an exemplary medical device or insertion device. When used herein, "proximal" refers to a position relatively closer to the exterior of the body or closer to an operator using the medical device or insertion device. In contrast, "distal" refers to a position relatively farther away from the operator using the medical device or insertion device, or closer to the interior of the body.

Both the foregoing general description and the following detailed description are exemplary and explanatory only and are not restrictive of the features, as claimed. As used herein, the terms "comprises," "comprising," "including," "having," or other variations thereof, are intended to cover a non-exclusive inclusion such that a process, method, article, or apparatus that comprises a list of elements does not include only those elements, but may include other elements not expressly listed or inherent to such a process, method, article, or apparatus. Additionally, the term "exemplary" is used herein in the sense of "example," rather than "ideal." As used herein, the terms "about," "substantially," and "approximately," indicate a range of values within +/−5% of the stated value.

Figure 1A:
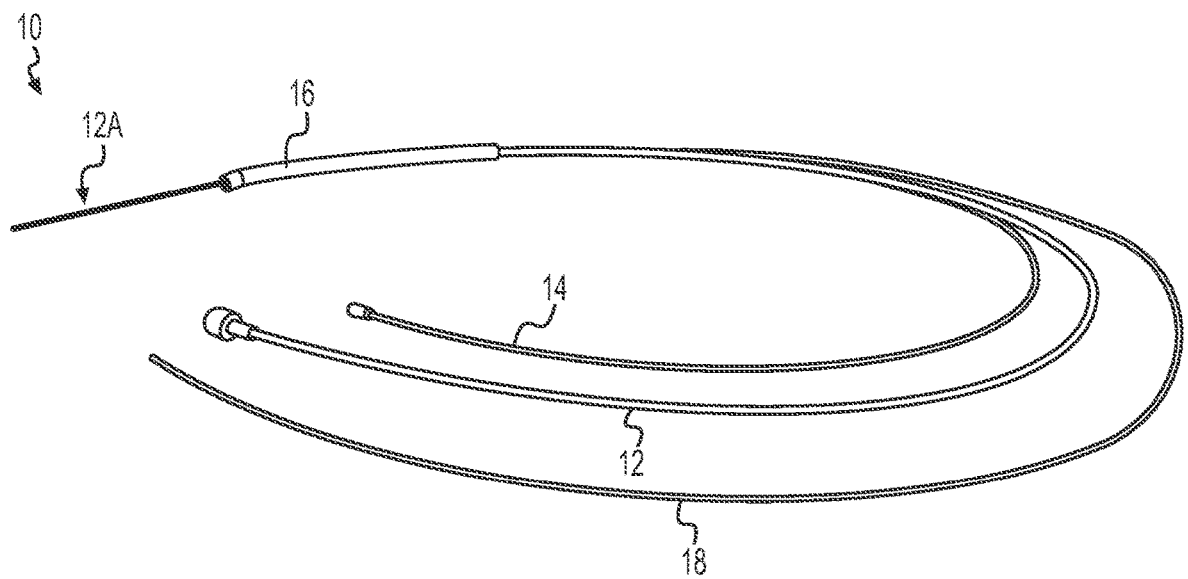
FIG. 1A illustrates a medical system, according to aspects of the present disclosure.
Figure 1B:
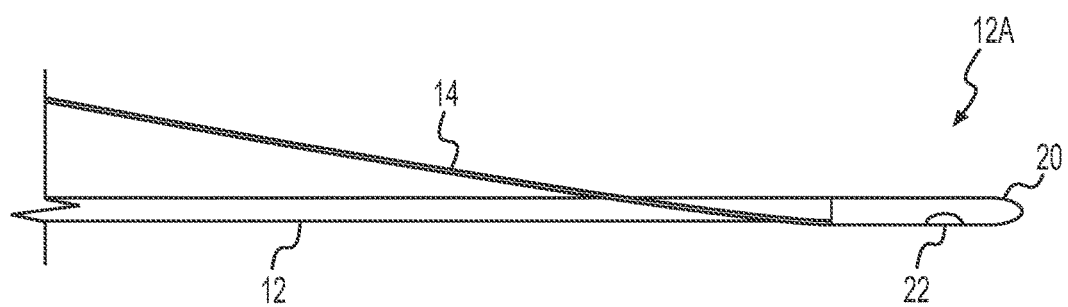
FIG. 1B illustrates a distal portion of the medical system of FIG. 1A.

FIG. 1A illustrates a medical system 10 that includes a laser fiber 12 and a wire 14 that may be inserted through an insertion device 16 to be delivered to a treatment site. Medical system 10 may also include a tube 18, for example, an irrigation tube for delivering a saline solution or a suction tube for removing liquid or materials. Although not shown, proximal portions of laser fiber 12, wire 14, and tube 18 may be connected to one or more controllers, energy or fluid sources, etc. Insertion device 16 may be a cystoscope or other appropriate insertion device, and may include one or more lumens in order for fiber 12, wire 14, and tube 18 to be inserted through the lumen(s) in order to reach the treatment site. As shown in FIGS. 1A and 1B, a distal portion 12A of laser fiber 12 may extend distally beyond insertion device 16.

Laser fiber 12 may be a fiber optic fiber, for example, a MoXy™ Fiber Optic by Boston Scientific Corp. Laser fiber 12 may deliver 532 nm laser energy from a compatible laser console to tissue during surgical procedures, including PVP to treat BPH. Laser fiber 12 may include one or more insulation layers, cladding layers, buffer layers, coatings, etc. in order to insulate and/or guide the energy being delivered through laser fiber 12. Laser fiber 12 may include a distal end cap 20. Distal end cap 20 may include a side opening 22 in order for laser fiber 12 to emit laser energy out of side opening 22 to form a side-fire distal end. For example, laser fiber 12 may deliver up to 180 W of 532 nm light toward the tissue through side opening 22 in distal end cap 20. Distal end cap 20 may be formed of a conductive material, for example, a metallic or conductive ceramic material. Alternatively, although not shown, distal end cap 20 may include a distal opening in order to deliver laser energy distally out of the distal opening to treat tissue.

Wire 14 may be a thin conductive wire (e.g., smaller than laser fiber 12), and may be formed of any appropriate conductive material, for example, a metallic material. Additionally, a proximal end of wire 14 may be coupled to an electrical energy source, for example, a RF current generator, to conduct the electrical energy. Wire 14 may include one or more coatings and/or layers of insulation in order to insulate and/or guide the energy being conducted by wire 14.

As shown in FIG. 1B, a distal portion of wire 14 may be coupled to distal portion 12A of laser fiber 12, for example, to distal end cap 20. In one aspect, the distal portion of wire 14 may be welded, soldered, or otherwise fixedly coupled to distal end cap 20. As a result, a user may deliver electrical energy to tissue by energizing the electrical energy source such that wire 14 conducts the energy and energizes distal end cap 20. The energized distal end cap 20 may be applied to the tissue, for example, to help cauterize and/or coagulate tissue to help stop or lessen bleeding. In this manner, the user may deliver laser energy to tissue via laser fiber 12 via side opening 22, and may then deliver electrical energy to the tissue via wire 14 and distal end cap 20. The application site(s) of the laser energy and of the electrical energy may be controlled by the position of distal end cap 20, for example, by extending or retracting laser fiber 12 relative to insertion device 16. Accordingly, the user may treat tissue with laser energy (i.e., evaporate) and also treat tissue with electrical energy (i.e., cauterize and/or coagulate) with without removing laser fiber 12 or wire 14 from an insertion device or otherwise moving the elements of system 10.

Figure 2A:
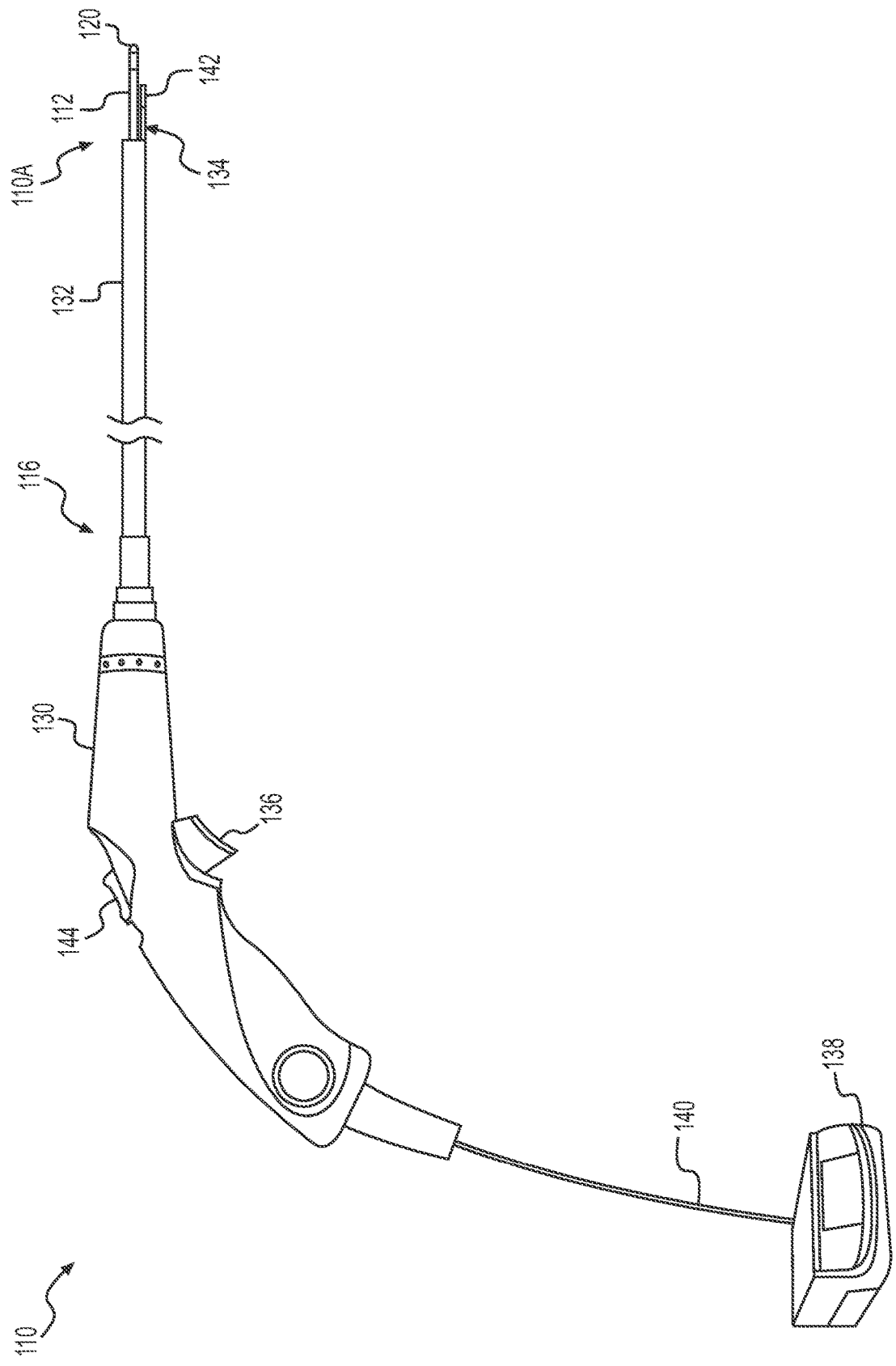
FIG. 2A illustrates another medical system, according to aspects of the present disclosure.

FIGS. 2A-2D illustrate an alternative example according to the present disclosure, with similar elements to medical system 10 shown by 100 added to the reference numbers. As shown in FIG. 2A, a medical system 110 includes an insertion device 116 with a laser fiber 112 extending therethrough. Insertion device 116 may be a cystoscope or another appropriate insertion device. Insertion device 116 may include a handle 130 and a delivery portion 132, which includes a distal extension 134. Distal extension 134 may include a conductive portion 142 (FIG. 2B), as discussed below. Handle 130 may include one or more actuators, for example, a trigger 136, and may also be coupled to one or more additional actuators, for example, a foot pedal 138, via a cable 140. The one or more actuators may control the delivery of laser energy to the tissue via laser fiber 112 and may also control the delivery of electrical energy to the tissue via conductive portion 142.

Figure 2B:
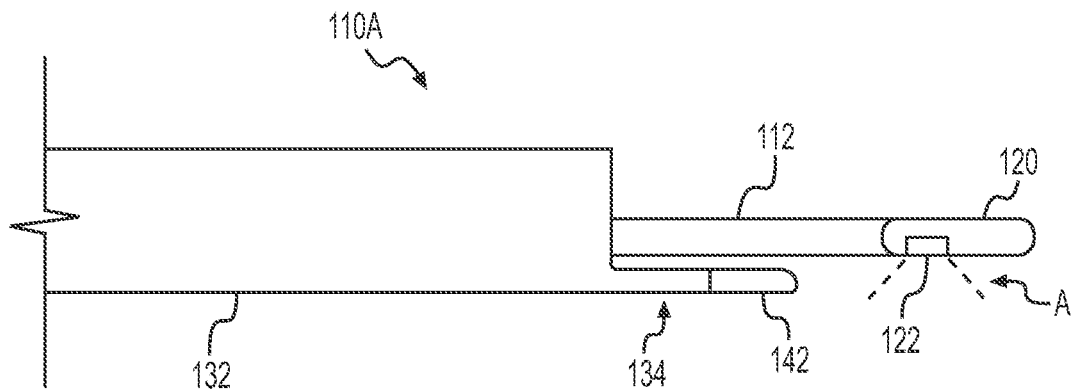
FIGS. 2B-2D are different views of a distal portion of the medical system of FIG. 2A in different configurations.
Figure 2C:
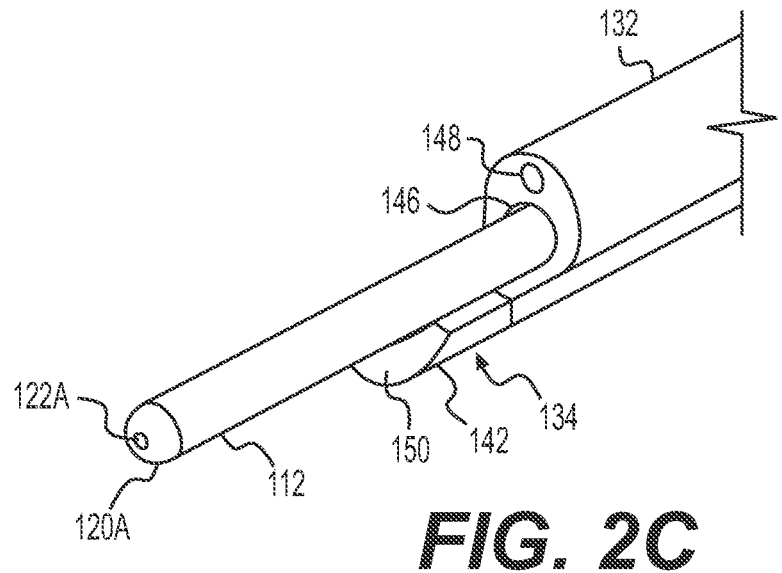
Figure 2D:
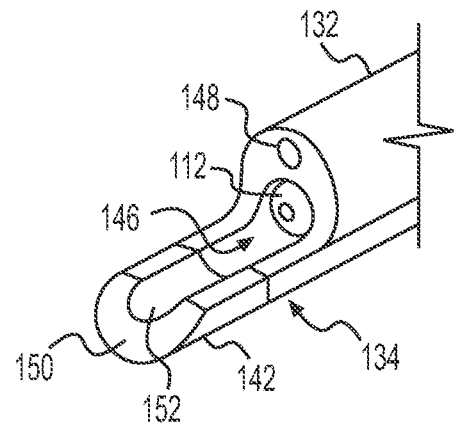

FIG. 2B is a side view of a distal portion 110A of medical system 110, and FIGS. 2C and 2D are perspective views of distal portion 110A in different configurations. As shown in FIG. 2B, laser fiber 112 and distal extension 134 extend distally from delivery portion 132. Laser fiber 112 may include a distal end cap 120, which may be a side-fire laser end cap with a side opening 122 to emit laser energy A, as discussed above. In an extended configuration as shown in FIG. 2B, laser fiber 112 may extend distally beyond distal extension 134 such that at least distal end cap 120 is distally beyond distal extension 134.

Distal extension 134 may include conductive portion 142, for example, at the distalmost end of distal extension 134. Conductive portion 142 may be formed of any appropriate material, for example, a metallic or partially metallic material, a conductive ceramic material, etc. As discussed above with respect to wire 14, conductive portion 142 may be coupled to an energy source (i.e., an RF energy source, which is not shown). For example, conductive portion 142 may be coupled to and energized via an internal conductive wire (not shown) extending through handle 130 and delivery portion 132. Conductive portion 142 may be energized and may be applied to tissue in order to help cauterize and/or coagulate the tissue. Additionally, conductive portion 142 may be electrically insulated from the remaining portion of distal extension 134 and delivery portion 132 in order to control the size or amount of tissue receiving electrical energy. In one aspect, conductive portion 142 may be formed of a conductive ceramic, and the remainder of distal extension 134 may be formed of a non-conductive ceramic.

FIG. 2C illustrates laser fiber 112 in an extended position, and FIG. 2D illustrates laser fiber 112 in a retracted position. Both FIGS. 2C and 2D illustrate laser fiber 112 with a distal end cap 120A that may allow for laser fiber 112 to serve as an end-fire laser fiber, for example, with a distal opening 122A, rather than the side-fire configuration with side opening 122. In either aspect, laser fiber 112 is movable relative to delivery portion 132 by extending or retracting laser fiber 112 relative to handle 130, by a longitudinal or rotational actuator on handle 130 (e.g., a slider 144 on handle 130), or any other appropriate control mechanism. Laser fiber 112 is movable within a laser lumen 146 through delivery portion 132. With laser fiber 112 in the extended position, laser energy may be emitted (either as a side-fire as shown in FIG. 2B or as an end-fire as shown in FIG. 2C) to treat (e.g., evaporate) tissue. With laser fiber 112 in the retracted position, electrical energy may be delivered to conductive portion 142, and conductive portion 142 may be applied to tissue to treat (e.g., cauterize or coagulate) the tissue. Accordingly, the user may treat tissue with laser energy (i.e., evaporate) and also treat tissue with electrical energy (i.e., cauterize and/or coagulate) with without removing laser fiber 112 or delivery portion 132 from treatment site, without inserting an additional electrode or element to the treatment site, and without otherwise moving the elements of system 110.

Additionally, delivery portion 132 may include one or more additional lumens (e.g., for irrigation, suction, etc.) and may include one or more visualization units 148 (e.g., cameras, illumination devices, etc.). Moreover, although laser fiber 112, delivery portion 134, and other components are shown as generally cylindrical, these components may take any appropriate shape.

In one aspect, distal extension 134 and conductive portion 142 may have a shape that may aid in pushing and/or adjusting the position of tissue, and may also aid in the insertion of medical system 110 to a treatment site. In this aspect, distal extension 134, including conductive portion 142, may include a rounded, angled, or otherwise atraumatic distal tip 150, and/or may include a "duckbill" shape with a narrow distalmost portion that widens in the proximal direction. Distal extension 134 may extend approximately 10 to 12 mm from the delivery portion 132, and conductive portion 142 may be approximately half the length of distal extension 134. In this aspect, conductive portion 142 may be within the range of a camera positioned within visualization unit 148. Conductive portion 142 and distal extension 134 may include a groove 152 that at least partially aligns with laser lumen 146 to accommodate and/or support a portion of laser fiber 112 when laser fiber 112 is in the extended position.

A user may move handle 130, and thus delivery portion 132, distal extension 134 and conductive portion 142, and distal tip 150 may be used to adjust the position of tissue being treated. In this aspect, distal tip 150 may contact the tissue being moved, and conductive portion 142 may be deenergized. Alternatively, conductive portion 142 may be energized, and distal tip 150 may be used to both move and treat (i.e., cauterize and/or coagulate) the tissue. For example, distal tip 150 may be used to move tissue during a PVP procedure or during an enucleation procedure to remove prostate tissue (e.g., where laser fiber 112 is a holmium laser fiber). In these aspects, a user may deliver laser energy (i.e., evaporate or enucleate) to tissue, may deliver electrical energy (i.e., cauterize and/or coagulate) to tissue, and/or adjust the position of tissue without removing laser fiber 112 or delivery portion 132 from treatment site, without inserting an additional electrode or element to the treatment site, and without otherwise moving the elements of system 110.

Figure 3A:
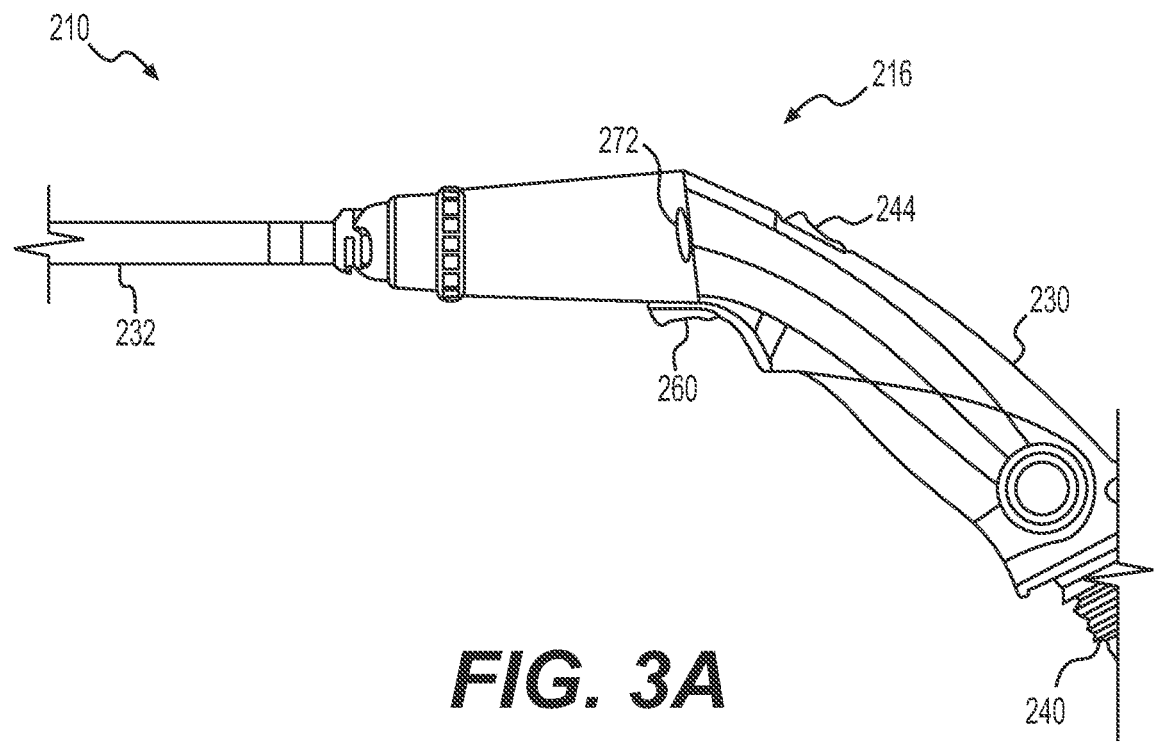
FIG. 3A illustrates a side view of yet another medical system, according to aspects of the present disclosure.
Figure 3B:
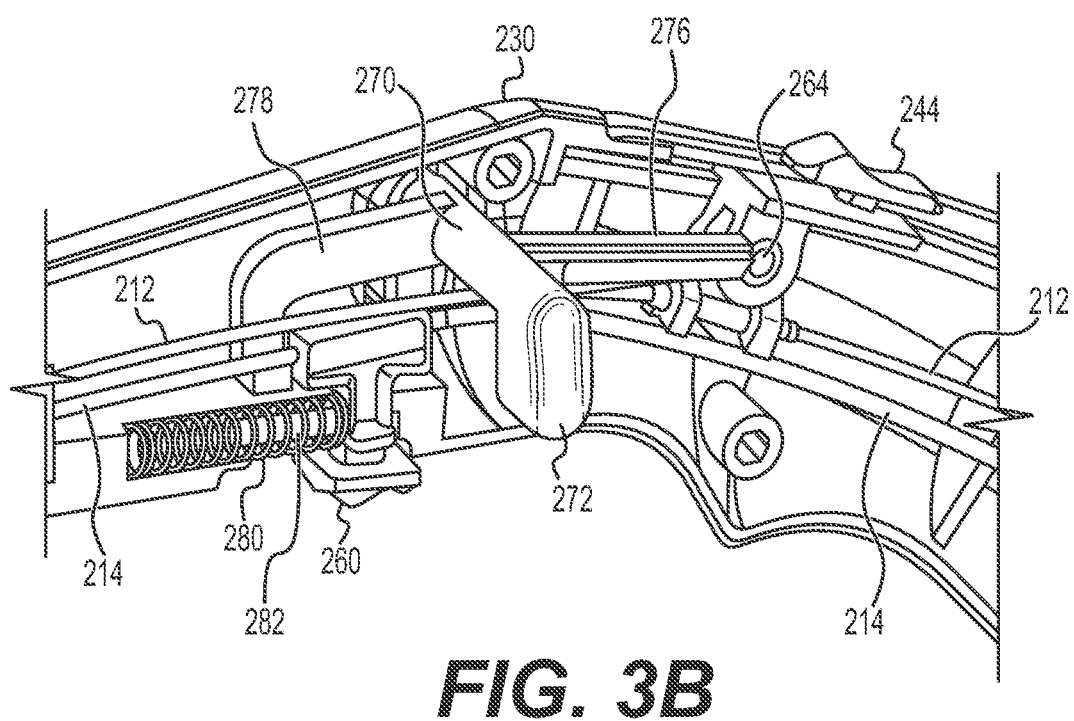
FIGS. 3B-3F illustrate cross-sectional and top views of portions of the medical system of FIG. 3A.

FIGS. 3A-3F illustrate an alternative example according to the present disclosure, with similar elements to medical system 10 shown by 200 added to the reference numbers. As shown in FIGS. 3A and 3B, a medical system 210 includes an insertion device 216 with a laser fiber 212 and a wire 214 extending therethrough. Wire 214 may include an electrode at a distal end, for example, a cautery and/or coagulation electrode.

Insertion device 216 may be a cystoscope or another appropriate insertion device. Insertion device 216 may include a handle 230 and a delivery portion 232. Although not shown, delivery portion 232 may include one or more lumens, for example, a first lumen to receive laser fiber 212 and a second lumen to receive wire 214. Handle 230 may include one or more actuators, for example, a trigger, and may also be coupled to one or more additional actuators, for example, a foot pedal via a cable 240 as discussed with respect to FIG. 2A. The one or more actuators may control the delivery of laser energy via laser fiber 212 and may also control the delivery of electrical energy via wire 214. For example, a foot pedal similar to foot pedal 138 of FIG. 2A may be coupled to handle 230 and may control the delivery of laser energy via laser fiber 212. Likewise, a trigger similar to trigger 136 of FIG. 2A may be positioned on handle 230 and may control the delivery of electrical energy via wire 214.

Additionally, handle 230 may include one or more sliders to control the extension and/or retraction of laser fiber 212 and wire 214. For example, a laser slider 244 may be coupled (either directly or indirectly) to a portion of laser fiber 212, and a wire slider 260 may be coupled (either directly or indirectly) to a portion of wire 214. Handle 230 may also include a lock 270 in order to help control the extension and/or retraction of laser fiber 212 and wire 214. For example, lock 270 may help prevent laser fiber 212 and wire 214 from both being extended distally from delivery portion 232 at the same time, as exposure to laser energy may damage wire 214 or the distal electrode coupled to wire 214. Similarly, exposure to electrical energy may damage laser fiber 212 and/or an end cap on laser fiber 212.

Laser slider 244 may be positioned on a top portion of handle 230, and is moveable relative to handle 230, for example, within a slot on handle 230. Laser slider 244 may be coupled to laser fiber 212 via a slider arm 264. For example, slider arm 264 may be coupled to and/or surround one or more portions of laser fiber 212, and movement of laser slider 244 forward or backward relative to handle 230 may move slider arm 264, and thus laser fiber 212, forward or backward relative to insertion device 216. Therefore, the movement of laser slider 244 on handle 230 may control the extension and/or retraction of laser fiber 212 relative to a distal end of delivery portion 232. Furthermore, it is noted that laser slider 244 may be coupled to and/or surround one or more portions of laser fiber 212 in any appropriate configuration (e.g., via a friction fit coupling, an adhesive coupling, a rocker arm coupling, etc.)

Wire slider 260 may be positioned on a bottom portion of handle 230, and is movable relative to handle 230, for example, within another slot on handle 230. Wire slider 260 may be coupled to and/or surround a portion of wire 214. Movement of wire slider 260 forward or backward relative to handle 230 may extend or retract wire 214 relative to insertion device 216. Furthermore, it is noted that wire slider 260 may be coupled to and/or surround one or more portions of wire 214 in any appropriate configuration (e.g., via a friction fit coupling, an adhesive coupling, a rocker arm coupling, etc.) Additionally, the movement of wire slider 260 in at least one direction (e.g., forward) may be biased by a spring 280. Wire slider 260 may include a rod 282 that extends forward from wire slider 260 within a portion of spring 280 in order to help retain spring 280. Additionally, rod 282 may limit the forward movement of wire slider 260, and thus of wire 214, by abutting an inner portion of handle 230 in a forward position (FIG. 3E).

Lock 270 may include two side arms 272 and 274 that may selectively extend from sides of handle 230 depending on the position of lock 270. Lock 270 may also include a rear arm 276 and a forward arm 278. Rear arm 276 and forward arm 278 may be laterally offset from one another. In this aspect, lock 270 may be positioned in at least two positions in order to selectively lock the movement of either laser slider 244 or wire slider 260.

Figure 3C:
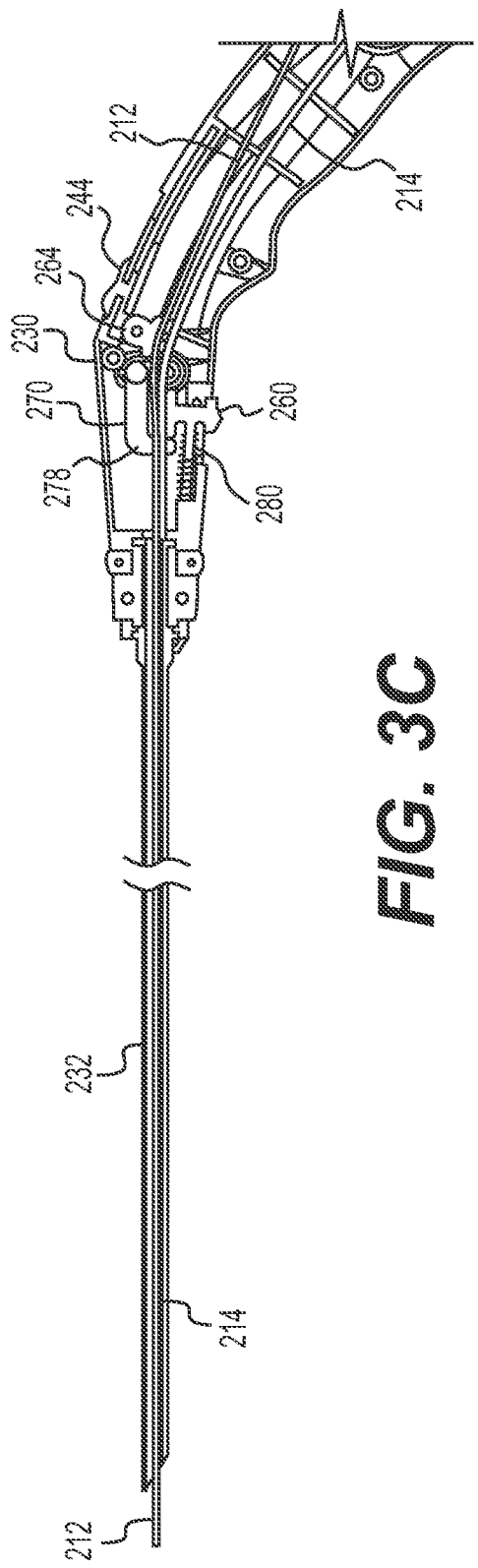
Figure 3D:
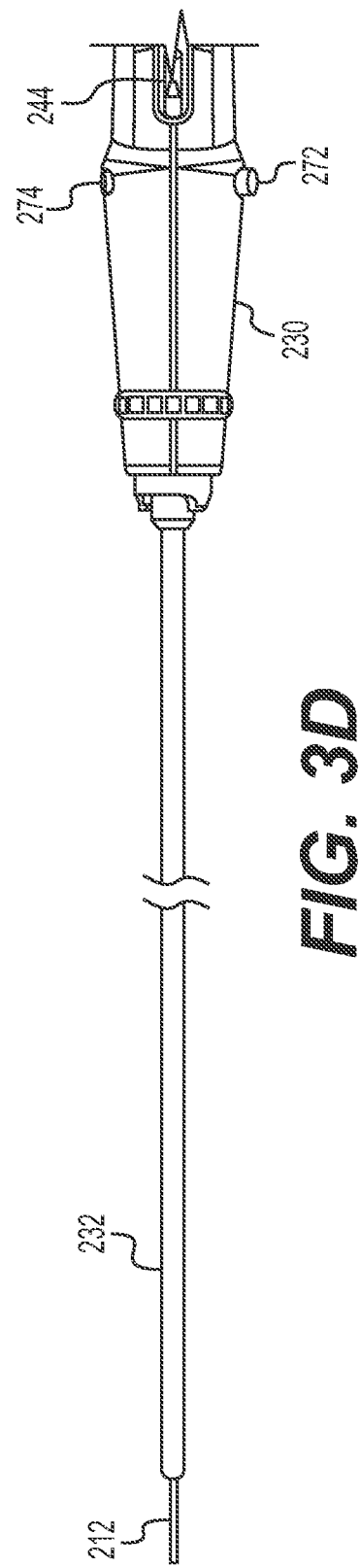

FIGS. 3C and 3D illustrate lock 270 in a first position, which may correspond to a lasing and/or evaporation mode. In this first position, lock 270 may block the movement of wire slider 260 such that wire 214 may not be extended from delivery portion 232, while laser slider 244 and laser fiber 212 may be extended and/or retracted. In this first position, first side arm 272 may extend from one side handle 230, and second side arm 274 may be retracted within or aligned with another side of handle 230 (FIG. 3D). Additionally, a rear portion of forward arm 278 may abut a forward portion of wire slider 260, thus blocking the movement of wire slider 260. In this configuration, the user may extend laser fiber 212 by extending laser slider 244 and deliver laser energy to treat the tissue, without the risk of wire 214 inadvertently being extended.

Figure 3E:
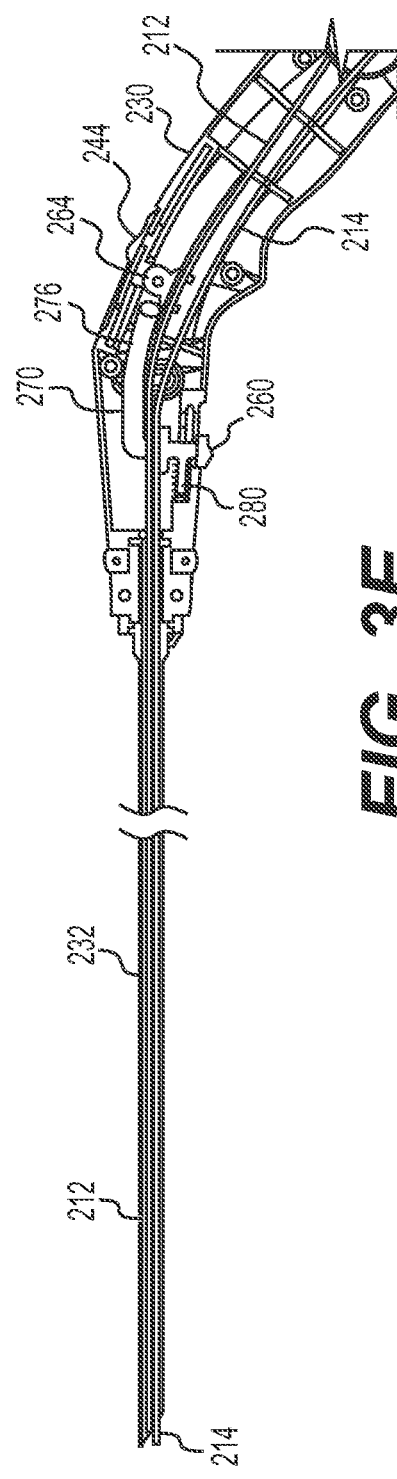
Figure 3F:
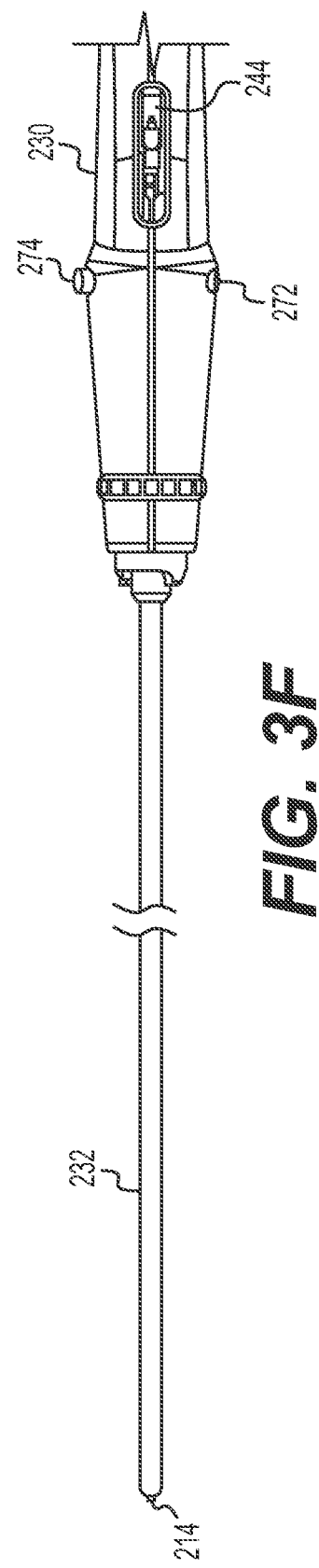

FIGS. 3E and 3F illustrate lock in a second position, which may correspond to a cautery and/or coagulation mode. In this second position, lock 270 may block the movement of laser slider 244 such that laser fiber 212 may not be extended from delivery portion 232, while wire slider 260 and wire 214 may be extended and/or retracted. Lock 270 may be moved from the first position to the second position by the user pushing first side arm 272 into handle 230. As a result, in the second position, second side arm 274 may extend from one side handle 230, and first side arm 272 may be retracted within or aligned with another side of handle 230 (FIG. 3F). Additionally, a rear portion of rear arm 276 may abut a forward portion of laser slider 244 and/or slider arm 264, thus blocking the movement of laser slider 244. In this configuration, the user may extend wire 214 by extending wire slider 260 and deliver electrical energy to treat the tissue, without the risk of laser fiber 212 inadvertently being extended.

As shown in FIGS. 3B and 3E, the extension of wire 214 may be biased by spring 280. As a result, the user may extend wire 214 distally via wire slider 260, but spring 260 biases wire slider 260 proximally such that wire 214 returns to a retracted position when the user removes the distal pressure on wire slider 260. Additionally, the extension may be limited by the engagement or abutment of rod 282 with an internal portion of handle 230. Accordingly, as shown in FIG. 3F, wire 214 may not be extended from delivery portion 232 as far as laser fiber 212 (FIG. 3D).

In some aspects, the movement of laser slider 244, and thus laser fiber 212, may not be biased. During a procedure, laser fiber 212 is often extended for a longer duration than wire 214, and the user may desire to maintain laser fiber 212 in an extended position without maintaining pressure on laser slider 244. Nevertheless, with laser slider 244 and laser fiber 212 extended proximally, laser slider 244 may be laterally adjacent to a portion of rear arm 276 in a longitudinal direction of handle 230. Accordingly, laser slider 244 may block rear arm 276, and thus lock 270, from moving from the first position (lasing mode) to the second position (cautery and/or coagulation mode). The user may move laser slider 244 to a distal position to retract laser fiber 212, and may then move lock from the first position to the second position to extend wire 214 and treat the tissue.

Medical system 210 may help to control the extension of laser fiber 212 and wire 214. For example, a user may deliver laser energy (i.e., evaporate) via laser fiber 212 and may deliver electrical energy (i.e., cauterize and/or coagulate) via wire 214 without removing laser fiber 212, wire 214, or delivery portion 232 from treatment site, without inserting an additional electrode or element to the treatment site, and without otherwise moving the elements of system 210. Additionally, lock 270 and spring 280 may help to prevent laser fiber 212 and wire 214 from being extended distally from delivery portion 232 at the same time. As mentioned above, wire 214 may include a distal electrode (e.g., a cautery and/or coagulation electrode), and wire 214 and/or the distal electrode may be damaged if exposed to laser energy from laser fiber 212.

Once delivery portion 232 is inserted to a treatment site, a user may position lock 270 in the first position (FIGS. 3C and 3D) by pushing second side arm 274 into handle 230 such that first side arm 272 extends from handle 230. In this position, forward arm 278 abuts a portion of wire slider 260. The user may then extend laser fiber 212 from delivery portion 232 by moving laser slider 244 distally. The user may deliver laser energy to the tissue by activating a laser source (e.g., via a trigger, a foot pedal, etc.) in order to evaporate tissue at the treatment site. In a situation where bleeding or other damage to the tissue occurs during the application of the laser energy, the user may position lock 270 in the second position (FIGS. 3E and 3F) by retracting laser slider 244 and pushing first side arm 272 into handle 230 such that second side arm 274 extends from handle 230. In this position, rear arm 276 abuts a portion of laser slider 244. The user may then extend wire 214 from delivery portion 232 by moving wire slider 260 distally. The user may deliver electrical energy to the tissue by activating an electrical energy source (e.g., via a trigger, a foot pedal, etc.) in order to cauterize and/or coagulate tissue at the treatment site. The user may retract wire 214 manually by moving wire slider 260, or spring 280 may automatically return wire slider 260 to a distal position. The user may then continue to treat the tissue at the treatment site by selectively positioning lock 270 in the first position or in the second position. Throughout any of the above steps, the user may reposition the distal end of delivery portion 232 in order to treat different areas of the treatment site.

While much of this disclosure is directed to treatment of prostate tissue, in particular to treat BPH, it is further contemplated that the systems and procedures discussed herein may be equally applicable to other medical procedures. For example, medical systems 10, 110, 210 may be used in any medical procedure that requires both laser energy and electrical energy. In one aspect, medical systems 10, 110, 210 may be used to delivery laser energy to kidney stones in a percutaneous nephrolithonomy ("PCNL") procedure and delivery electrical energy to cauterize and/or coagulate any tissue that becomes damage during the laser energy delivery. The systems and methods discussed above may also be used in procedures to break up and/or treat ureteral stones, gallstones, bile duct stones, polyps, etc. Moreover, medical system 210 may be used in any medical procedure that requires two different energy delivery devices, where exposure to the first energy may damage the second energy deliver device.

While principles of the present disclosure are described herein with reference to illustrative examples for particular applications, it should be understood that the disclosure is not limited thereto. Those having ordinary skill in the art and access to the teachings provided herein will recognize additional modifications, applications, embodiments, and substitution of equivalents all fall within the scope of the features described herein. Accordingly, the claimed features are not to be considered as limited by the foregoing description.

We claim:

1. A medical system comprising:
an insertion device including a handle and a delivery portion;
a laser fiber, wherein the laser fiber extends through the insertion device and is coupled to a laser slider to control a position of the laser fiber relative to a distal end of the delivery portion;
a conductive wire, wherein the conductive wire extends through the insertion device and is coupled to a wire slider to control a position of the conductive wire relative to a distal end of the delivery portion; and
a lock positioned within the handle, wherein the lock is movable in order to selectively lock either movement of the laser slider or movement of the wire slider, wherein the lock includes a first side arm, a second side arm, a forward arm, and a rear arm, wherein the forward arm and the rear arm are laterally offset from one another,
wherein, in a first configuration, the first side arm extends from a first side of the handle and the second side arm is within or aligned with a second side of the handle opposite to the first side, and the forward arm of the lock blocks the wire slider from moving distally in order to limit distal movement of the conductive wire and allows the laser slider and the laser fiber to move distally, and
wherein, in a second configuration, the second side arm extends from the second side of the handle and the first side arm is within or aligned with the first side of the handle, and another portion of the lock blocks the laser slider from moving distally in order to limit distal movement of the laser fiber and allows the wire slider and the conductive wire to move distally.

2. The medical system of claim 1, wherein in the second configuration, the rear arm blocks the laser slider from moving distally in order to limit distal movement of the laser fiber and allows the wire slider and the conductive wire to move distally.

3. The medical system of claim 2, further including a spring within the handle to bias distal movement of the wire slider.

4. The medical system of claim 3, wherein the wire slider includes a rod portion that extends distally through a portion of the spring, and wherein the rod portion limits the distal movement of the wire slider.

5. The medical system of claim 1, wherein the laser fiber includes a distal end cap to direct laser energy.

6. The medical system of claim 5, wherein the distal end cap includes a side opening to form a side-fire distal end.

7. The medical system of claim 1, wherein the laser slider is movably positioned on a top portion of the handle, and wherein the wire slider is movably positioned on a bottom portion of the handle.

8. The medical system of claim 1, further comprising:
a laser energy source; and
an electrical energy source,
wherein a proximal end of the laser fiber is configured to be coupled to the laser energy source, and
wherein a proximal end of the conductive wire is configured to be coupled to the electrical energy source.

9. The medical system of claim 8, further including:
a first actuator configured to control delivery of laser energy from the laser energy source to the laser fiber; and
a second actuator configured to control delivery of electrical energy from the electrical energy source to the conductive wire.

10. The medical system of claim 9, wherein the laser fiber is configured to deliver up to 180 W of 532 nm light.

11. A medical device, comprising:
a handle,
a delivery portion extending from the handle;
a first slider movably coupled to the handle and configured to control movement of a first energy delivery device;
a second slider movably coupled to the handle and configured to control movement of a second energy delivery device; and
a lock at least partially positioned within the handle, wherein the lock includes a first side arm, a second side arm, a forward arm, and a rear arm, wherein the forward arm and the rear arm are laterally offset from one another,
wherein the lock is movable between a first position in which the forward arm of the lock blocks distal movement of the first slider in order to limit distal movement of the first energy delivery device and allows the second slider and the second energy delivery device to move distally, and a second position in which the rear arm of the lock blocks distal movement of the second slider in order to limit the distal movement of the second energy delivery device and allows the first slider and the first energy delivery device to move distally, and
wherein, in the first position, the first side arm extends from a first side of the handle and the second side arm is within or aligned with a second side of the handle opposite to the first side, wherein, in the second position, the second side arm extends from the second side of the handle and the first side arm is within or aligned with the first side of the handle.

12. The medical device of claim 11, further comprising a spring coupled to a distal end of the second slider to bias the distal movement of the second slider.

13. A method of delivering treatment to a treatment site, comprising:
positioning a distal end of a delivery portion of a medical device at the treatment site, wherein the delivery portion is coupled to a handle that includes:
a laser slider coupled to a laser fiber and controllable to extend or retract the laser fiber from the distal end of the delivery portion;
a wire slider coupled to a conductive wire and controllable to extend or retract the conductive wire from the distal end of the delivery portion; and
a lock, wherein the lock is movable to selectively limit distal movement of one of either the laser slider or the wire slider, and wherein the lock includes a first side arm, a second side arm, a forward arm, and a rear arm, wherein the forward arm and the rear arm are laterally offset from one another;
positioning the lock in a first position in which the forward arm of the lock blocks the distal movement of the wire slider, wherein, in the first position, the first side arm extends from a first side of the handle and the second side arm is within or aligned with a second side of the handle opposite to the first side;
extending the laser fiber by moving the laser slider distally;
delivering laser energy to the treatment site through the laser fiber to vaporize tissue;
retracting the laser fiber by moving the laser slider proximally;
positioning the lock in a second position in which the rear arm of the lock blocks the distal movement of the laser slider, wherein, in the second position, the second side arm extends from the second side of the handle and the first side arm is within or aligned with the first side of the handle;
extending the conductive wire by moving the wire slider distally; and
delivering electrical energy to the treatment site through the conductive wire to cauterize or coagulate tissue.

* * * * *